United States Patent [19]
Molt

[11] 3,970,678
[45] July 20, 1976

[54] ORGANOTIN MERCAPTIDE PROCESS

[75] Inventor: Kenneth R. Molt, Montgomery, Ohio

[73] Assignee: Cincinnati Milacron Chemicals, Inc., Reading, Ohio

[22] Filed: Mar. 8, 1974

[21] Appl. No.: 449,435

[52] U.S. Cl. .................. 260/429.7; 260/45.75 S
[51] Int. Cl.² ........................................ C07F 7/22
[58] Field of Search ............................ 260/429.7

[56] References Cited
UNITED STATES PATENTS

| | | | |
|---|---|---|---|
| 2,809,956 | 10/1957 | Mack et al. | 260/429.7 X |
| 3,475,472 | 10/1969 | Suzuki et al. | 260/429.7 |
| 3,478,071 | 11/1969 | Weisfeld | 260/429.7 |
| 3,507,893 | 4/1970 | Reifenberg | 260/429.7 |
| 3,542,825 | 11/1970 | Hoye | 260/429.7 |
| 3,565,930 | 2/1971 | Kauder et al. | 260/429.7 |
| 3,565,931 | 2/1971 | Brecker | 260/429.7 |
| 3,651,015 | 3/1972 | Ishida et al. | 260/429.7 X |
| 3,660,443 | 5/1972 | Boissieras et al. | 260/429.7 |
| 3,665,025 | 5/1972 | Wowk | 260/429.7 |
| 3,758,341 | 9/1973 | Wowk | 260/429.7 |
| 3,758,537 | 9/1973 | Wowk | 260/429.7 |
| 3,775,451 | 11/1973 | Brecker | 260/429.7 |
| 3,778,456 | 12/1973 | Hoye et al. | 260/429.7 |
| 3,869,487 | 3/1975 | Kugele et al. | 260/429.7 |

*Primary Examiner*—Helen M. S. Sneed
*Attorney, Agent, or Firm*—Cushman, Darby & Cushman

[57] ABSTRACT

The following reactions are carried out in the presence of aprotic solvents as catalysts:

(1)

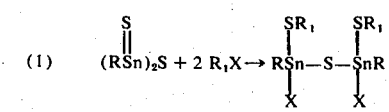

(2)

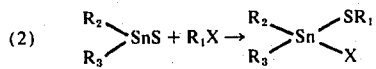

(3)

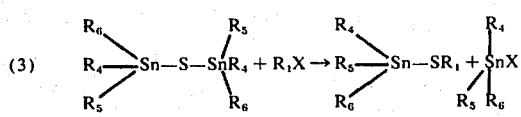

(4)

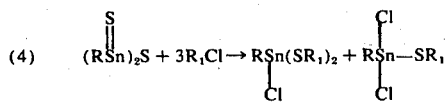

where R, $R_2$, $R_3$, $R_4$, $R_5$, and $R_6$ are alkyl, cycloalkyl, alkenyl, aryl or aralkyl, $R_1$ is

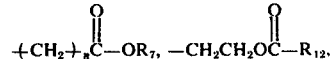

allyl, methallyl or benzyl, $R_7$ is alkyl, cycloalkyl, alkenyl or aralkyl, $R_{12}$ is alkyl or alkenyl, X is chlorine or bromine and n is 1 or 2. The aprotic solvents are (a)

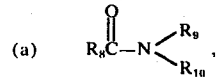

(b)

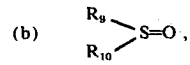

(c) 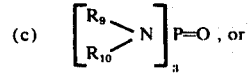 , or (d) N-methyl-2-pyrrolidone where $R_8$ is H or $CH_3$ and $R_9$ and $R_{10}$ are $CH_3$ or $C_2H_5$.

19 Claims, No Drawings

ORGANOTIN MERCAPTIDE PROCESS

The present invention is directed to a new method of preparing organotin mercaptides. It is based on the reaction of organotin sulfides with active organic halides in the presence of specific aprotic solvents. The reactions involved are as follows:

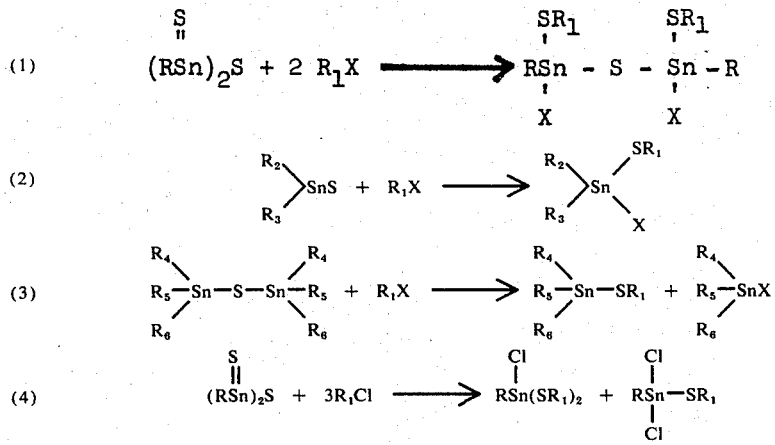

where R, $R_2$, $R_3$, $R_4$, $R_5$, and $R_6$ are alkyl, usually of 1 to 20 carbon atoms, cycloalkyl, usually of 5 to 6 carbon atoms in the ring, alkenyl, usually of 2 to 20 or more frequently 3 to 18 carbon atoms, aryl, usually phenyl or alkyl phenyl having 1 to 4 carbon atoms in the alkyl group, or aralkyl, usually of 7 carbon atoms; $R_1$ is

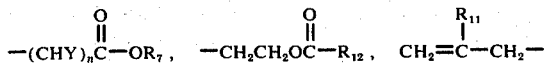

where $R_{11}$ is hydrogen or methyl $R_7$ is alkyl usually of 1 to 20 carbon atoms, cycloalkyl usually having 5 to 6 carbon atoms in the ring, alkenyl, usually of 2 to 20 carbon atoms, more commonly 3 to 18 carbon atoms, or aralkyl, usually of 7 carbon atoms, $R_{12}$ is alkyl, usually of 1 to 19 carbon atoms, or alkenyl, usually of 2 to 17 carbon atoms, X is a halogen of atomic weight 35 to 80, i.e., chlorine or bromine, $n$ is an integer of 1 to 2, one Y is chlorine or bromine and any other Y is hydrogen. As the aprotic solvents employed as catalysts there are used:

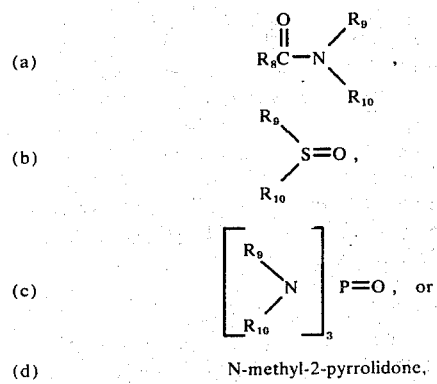

(d)     N-methyl-2-pyrrolidone, where $R_8$ is hydrogen or methyl and $R_9$ and $R_{10}$ are methyl or ethyl. The preferred catalyst is dimethyl formamide. The amount of catalyst is not especially critical and can vary for example from 0.1 to 10 moles per mole of organotin sulfide, preferably 0.8 to 8 moles per mole of the organotin sulfide.

It is critical to use the catalyst since in the absence of the catalyst degradation reactions predominate and little or no product is formed.

As catalysts there can be used for example dimethyl formamide, dimethyl acetamide, diethyl formamide, diethyl acetamide, dimethyl sulfoxide, diethyl sulfoxide, tris(dimethylamino) phosphine oxide, tris(diethylamino) phosphine oxide and N-methyl-2-pyrrolidone.

As compounds of the formula $R_1X$ there can be used methyl chloroacetate, methyl bromoacetate, ethyl chloroacetate, propyl chloroacetate, propyl bromoacetate, butyl chloroacetate, butyl bromoacetate, hexyl chloroacetate, hexyl bromoacetate, octyl chloroacetate, octyl bromoacetate, isooctyl chloroacetate, isooctyl bromoacetate, 2-ethylhexyl chloroacetate, 2-ethylhexyl bromoacetate, isodecyl chloroacetate, isodecyl bromoacetate, decyl chloroacetate, decyl bromoacetate, dodecyl chloroacetate, dodecyl bromoacetate, hexadecyl chloroacetate, hexadecyl bromoacetate, octadecyl chloroacetate, octadecyl bromoacetate, eicosanyl chloroacetate, eicosanyl bromoacetate, cyclopentyl chloroacetate, cyclopentyl bromoacetate, cyclohexyl chloroacetate, cyclohexyl bromoacetate, benzyl chloroacetate, benzyl bromoacetate, vinyl chloroacetate, vinyl bromoacetate, allyl chloroacetate, allyl bromoacetate, methallyl chloroacetate, methallyl bromoacetate, crotyl chloroacetate, crotyl bromoacetate, oleyl chloroacetate, oleyl bromoacetate, 2-chloroethyl acetate, 2-bromoethyl acetate, 2-chloroethyl propionate, 2-bromoethyl propionate, 2-chloroethyl butyrate, 2-bromoethyl butyrate, 2-chloroethyl valerate, 2-bromoethyl valerate, 2-chloroethyl pivalate, 2-bromoethyl pivalate, 2-chloroethyl caproate, 2-bromoethyl caproate, 2-chloroethyl octoate, 2-bromoethyl octoate, 2-chloroethyl decanoate, 2-bromoethyl decanoate, 2-chloroethyl laurate, 2-bromoethyl laurate, 2-chloroethyl palmitate, 2-bromoethyl palmitate, 2-chloroethyl stearate, 2-bromoethyl stearate, 2-chloroethyl eicosanate, 2-bromoethyl eicosanate, 2-chloroethyl acrylate, 2-bromoethyl acrylate, 2-chloroethyl methacrylate, 2-bromoethyl methacrylate, 2-chloroethyl crotonate, 2-bromoethyl crotonate, 2-chloroethyl oleate, 2-bromoethyl oleate, allyl chloride, allyl bromide, methallyl chloride, methallyl bromide, benzyl chloride, benzyl bromide, methyl 2-chloropropionate, methyl 2-bromopropionate, methyl 3-chloropropionate, methyl 3-bromopropionate, ethyl 2-chloropropionate, ethyl 2-bromopropionate, ethyl 3-chloropropionate, ethyl 3-bromopropionate, propyl 2-chloropropionate, propyl 3-bromopropionate, butyl 2-bromopropionate, butyl 3-chloropropionate, octyl 2-chloropropionate, octyl 3-chloropropionate, octyl 2-bromopropionate, octyl 3-bromopropionate, isooctyl 2-chloropropionate, isooctyl 2-bromopropionate, isooctyl 3-bromopropionate, isodecyl 2-chloropropionate, isodecyl 2-bromopropoionate, isodecyl 3-chloropropionate, n-decyl 3-bromopropionate, dodecyl 2-chloropropionate, tetradecyl 3-chloropropionate, hexadecyl 2-chloropropionate, hexadecyl 3-chloropropionate, octadecyl 2-chloropropionate, octadecyl 3-chloropropionate, octadecyl 2-bromopropionate, octadecyl 3-bromopropionate, 2-ethylhexyl 3-chloprioionate, 2-ethylhexyl 2-chloropropionate, eicosanyl 3-chloropropionate, cyclohexyl 2-chloropropionate, cyclohexyl 3-bromopropionate, cyclohexyl 3-chloropropionate, benzyl 2-chloropropionate, benzyl 3-chloropropionate, benzyl 2-bromopropionate, vinyl 2-chloropropionate, vinyl 3-bromopropionate, allyl 2-chloropropionate, allyl 3-chloropropionate, allyl 2-bromopropionate, allyl 3-bromopropionate, methallyl 3-chloropropionate, crotyl 2-chloropropionate, oleyl 2-chloropropionate, oleyl 3-chloropropionate, oleyl 2-bromopropionate, oleyl 3-bromopropionate.

Examples of starting materials of the formula

are monomethyltin sulfide, monoethyltin sulfide, monobutyltin sulfide, monooctyltin sulfide, monododecyltin sulfide, monooctadecyltin sulfide, monoeicosanyltin sulfide, monocyclohexyltin sulfide, monocyclopentyltin sulfide, monovinyltin sulfide, mono-2-ethylhexyltin sulfide, monoallyltin sulfide, monomethallyltin sulfide, monooleyltin sulfide, monophenyltin sulfide, mono-p-tolyltin sulfide, mono-p-butylphenyltin sulfide, monobenzyltin sulfide, Examples of starting materials within the formula

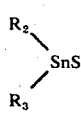

are dimethyltin sulfide, diethyltin sulfide, methyl butyltin sulfide, dipropyltin sulfide, dibutyltin sulfide, dihexyltin sulfide, dioctylin sulfide, di-2-ethylhexyltin sulfide, diisooctyltin sulfide, bis(dodecyltin) sulfide, bis(octadecyltin) sulfide, bis(eicosanyltin) sulfide, bis(cyclohexyltin) sulfide, divinyltin sulfide, diallyltin sulfide, dimethallyltin sulfide, dicrotyltin sulfide, dioleyltin sulfide, diphenyltin sulfide, mono-methyl-mono-phenyltin sulfide, di-p-tolyltin sulfide, di-p-butylphenyltin sulfide, dibenzyltin sulfide.

Examples of starting materials within the formula

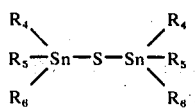

are: bis (trimethyltin) sulfide, bis(trimethyltin) sulfide, bis(tributyltin) sulfide, bis(trioctyltin) sulfide, bis(trioctadecyltin) sulfide, bis(trivinyltin) sulfide, bis(triallyltin) sulfide, bis(trimethallyltin) sulfide, bis(trioleyltin) sulfide, bis(triphenyltin) sulfide, bis (tri-p-tolyltin) sulfide, bis(tribenzyltin) sulfide.

Many of the products prepared in the present invention are old. Thus, Leistner U.S. pat. No. 2,641,596 discloses some of the non-chlorine containing compounds prepared by reaction (3). Brecker U.S. Pat. No. 3,565,931 shows many compounds which can be prepared from the compounds made by reaction (1). Hoye U.S. Pat. No. 3,542,825 discloses many compounds prepared by reaction (2) and (4) as does the similar British Pat. No. 1,117,652. Wowk U.S. Pat. No. 3,665,025 and British Pat. No. 1,297,550 disclose some of the compounds prepared by reaction (4) as well as compounds somewhat similar to those prepared in reaction (1).

The organotin mercaptides prepared by reactions (1), (2), (3) and (4) are useful for the same purposes as Leistner, Brecker U.S. Pat. No. 3,565,931, Brecker U.S. Pat. No. 3,630,992, Hoye, Wowk or British Patents No. 1,117,652 and British Patent No. 1,297,550. They are particularly useful not only as stabilizers but as intermediates for making stabilizers for polyvinyl chloride resins by replacing the halogen atom or atoms with oxygen, carboxyl, mercaptyl, or ester mercaptyl; they are also less expensive than organotin mercaptides prepared from mercaptans and organotin oxides or halides.

The organotin mercaptide stabilizers prepared in reactions (1), (2) and (3) of the present invention can be used with halogen containing vinyl and vinylidene resins in which the halogen is attached directly to the carbon atoms. Preferably, the resin is a vinyl halide resin, more particularly, a vinyl chloride resin. Usually, the vinyl chloride resin is made from monomers consisting of vinyl chloride alone or a mixture of monomers comprising at least 70% vinyl chloride by weight. When vinyl chloride copolymers are stabilized, preferably the copolymer of vinyl chloride with an ethylenically unsaturated compound copolymerizable therewith contains at least 10% of polymerized vinyl chloride.

As the halogen resin there can be employed chlorinated polyethylene having 14 to 75%, e.g., 27% chlorine by weight, polyvinyl chloride, polyvinylidene chloride, polyvinyl bromide, polyvinyl fluoride, polyvinylidene fluoride, copolymers of vinyl chloride with 1 to 90%, preferably, 1 to 30% of a copolymerizable ethylenically unsaturated material such as vinyl acetate, vinyl butyrate, vinyl benzoate, vinylidene chloride, diethyl fumarate, diethyl maleate, other alkyl fumarates and maleates, vinyl propionate, methyl acrylate, 2-ethylhexyl acrylate, butyl acrylate and other alkyl acrylates, methyl methacrylate, ethyl methacrylate, butyl methacrylate and other alkyl methacrylates, methyl alpha chloroacrylate, styrene, trichloroethylene, vinyl ethers such as vinyl ethyl ether, vinyl chloroethyl ether and vinyl phenyl ether, vinyl ketones such as vinyl methyl ketone and vinyl phenyl ketone, 1-fluoro-1-chloroethylene, acrylonitrile, chloroacrylonitrile, allylidene diacetate and chloroallylidene diacetate. Typical copolymers include vinyl chloride-vinyl acetate (96.4 sold commercially as VYNW), vinyl chloride-vinylacetate (87:13), vinyl chloride-vinyl acetate-Maleic anhydride (86:13:1), vinyl chloride-vinylidene chloride (95:5), vinyl chloride-diethyl fumarate (95:5), vinyl chloride-trichloroethylene (95:5), vinyl chloride-2-ethylhexyl acrylate (80:20).

The stabilizers of the present invention can be incorporated with the resin by admixing in an appropriate mill or mixer or by any of the other well-known methods which provide for uniform distribution throughout the resin compositions. Thus, mixing can be accomplished by milling on rolls at 100–160° C.

In addition to the novel stabilizers there can also be incorporated with the resin conventional additives such as plasticizers, pigments, fillers, dyes, ultraviolet light absorbing agents, densifying agents and the like.

If a plasticizer is employed, it is used in conventional amount, e.g., 30 to 150 parts per 100 parts of resin. Typical plasticizers are di-2-ethylhexyl phthalate, dibutyl sebacate, dioctyl sebacate, tricresyl phosphate.

The tin containing stabilizers are normally used in an amount of 0.01 to 10% by weight of the resin, more preferably 0.1 to 5% of the tin compound is used by weight of the resin. The organotin mercaptide products of reactions (1) (2) and (3) are clear, mobile liquids that are soluble in hydrocarbon and polar solvents such as benzene, toluene, acetone, and ethyl acetate. the mono- and di-organotin sulfides used as starting materials in reactions (1) and (2) are polymeric, high-melting solids and are insoluble in the reaction products and in most solvents that dissolve the reaction products. It is evident therefore, that the reaction products are not mere solutions of the organotin sulfides.

Specific combinations of organotin sulfides and $R_1X$ compounds in addition to those set forth in the working examples and mentioned as illustrative only and not as limiting are given below. The numbers indicate the number of moles of catalyst (and in reaction 1, also the moles of other reactant) per mole of starting sulfide.

REACTION (1)

1. Monomethyltin sulfide + 2 methyl chloroacetate + 4 dimethyl formamide (catalyst)
2. monooctyltin sulfide + 2 methyl bromoacetate + 4 dimethyl acetamide (catalyst)
3. monooctadecyltin sulfide + 2 isodecyl chloroacetate + 4 diethyl formamide (catalyst)
4. monobenzyltin sulfide + 2 butyl chloroacetate + 4 diethyl sulfoxide (catalyst)
5. monophenyltin sulfide + 2 cyclohexyl chloroacetate + 4 dimethyl sulfoxide (catalyst)
6. monoallyltin sulfide + 2 benzyl chloroacetate + 4 tris (diethylamino) phosphine oxide (catalyst)
7. monomethyltin sulfide + 2 2-chloroethyl stearate + 4 tri(diethylamino) phosphine oxide (catalyst)
8. monobutyltin sulfide + 2 2-chloroethyl oleate + 4 dimethyl formamide (catalyst)
9. monocyclohexyltin sulfide + 2 2-chloroethyl acetate + 4 dimethyl formamide (catalyst)
10. monomethyltin sulfide + 2 2-chloroethyl methacrylate + 4 dimethyl formamide (catalyst)
11. monomethyltin sulfide + 2 dodecyl 3-chloropropionate + 4 N-methyl pyrrolidone (catalyst)
12. monobutyltin sulfide + 2 allyl chloride + 5 dimethyl formamide (catalyst)

REACTION (2)

13. dimethyltin sulfide + ethyl chloroacetate + 2.5 dimethyl formamide (catalyst)
14. dibenzyltin sulfide + propyl bromoacetate + 2 dimethyl formamide (catalyst)
15. dioctyltin sulfide + decyl chloroacetate + 2 dimethyl formamide (catalyst)
16. dibutyltin sulfide + sec. butyl chloroacetate + 2 dimethyl sulfoxide (catalyst)
17. di-p-tolyltin sulfide + cyclohexyl bromoacetate + 4 dimethyl formamide (catalyst)
18. dioleyltin sulfide + phenethyl chloroacetate + 4.5 dimethyl acetamide (catalyst)
19. dimethyltin sulfide + 2-chloroethyl palmitate + 3 dimethyl sulfoxide (catalyst)
20. dibutyltin sulfide + 2-bromoethyl crotonate + 2 tris (dimethylamino) phosphine oxide (catalyst)
21. dicyclohexyltin sulfide + 2-chloroethyl pivalate + 2 dimethyl formamide (catalyst)
22. dimethyltin sulfide + 2-chloroethyl acrylate + 2 N-methyl pyrrolidone (catalyst)
23. dimethyltin sulfide + isooctyl 3-bromopropionate + 2 dimethyl formamide (catalyst)
24. dibutyltin sulfide + methallyl bromide + 1.5 dimethyl formamide (catalyst)

REACTION (3)

25. bis(trimethyltin) sulfide + isopropyl chloroacetate + 3 dimethyl formamide (catalyst)
26. bis(tribenzyltin) sulfide + 2-ethylhexyl chloroacetate + 2 dimethyl formamide (catalyst)
27. bis(trioctyltin) sulfide + nonyl bromoacetate + 4 dimethyl formamide (catalyst)
28. bis(tributyltin) sulfide + hexyl chloroacetate + 3 dimethyl sulfoxide (catalyst)
29. bis(triphenyltin) sulfide + isooctyl chloroacetate + 3 dimethyl formamide (catalyst)
30. bis(triallyltin sulfide) + benzyl chloroacetate + 3.3 dimethyl formamide (catalyst)
31. bis(trimethyltin) sulfide + 2-chloroethyl eicosanate + 3 dimethyl sulfoxide (catalyst)
32. bis(tributyltin)sulfide + bromoethyl methacrylate + 3 tris(dimethylamino) phosphine oxide (catalyst)
33. bis(tricyclohexyltin) sulfide + 2-chloroethyl myristate + 3 dimethyl formamide (catalyst)
34. bis(trimethyltin) sulfide + 2-bromoethyl oleate + 3 N-methyl pyrrolidone (catalyst)
35. bis(trimethyltin)sulfide + dodecyl 3-chloropropionate + 3 dimethyl formamide (catalyst)
36. bis(tributyltin) sulfide + allyl chloride + 3 dimethyl formamide (catalyst)

The temperature is not critical but is preferably between 130°–155° C. The temperature is usually between 100° C. and the boiling point of the catalyst. All of the catalysts are liquids at the reaction temperatures.

EXAMPLE 1

One-half mole of dimethyltinsulfide was mixed with 0.5 M of isooctylchloroacetate and 75.0 grams of dimethylformamide and heated to 130°–135° C. for 2 hours. Dimethylformamide was distilled from the reaction mixture by heating to a final pot temperature of 110° C. at 10 mm Hg. The residue (product) was clarified by filtration yielding 188.5 gms (97.3% of theoretical) of pale yellow oil. It is soluble in heptane and acetone. An NMR spectrum of the product was consistent with expected structure:

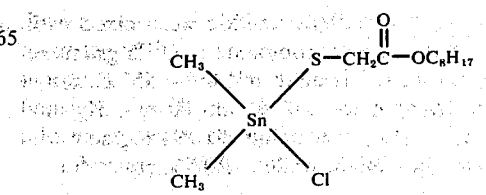

Cl— 9.2% (calculated 9.16%)
S — 8.4% (calculated 8.26%)

EXAMPLE 2

One-half mole of monomethyltin sulfide $(CH_3SnS)_2S$ was mixed with 1.0 M of isooctylchloroacetate and 150 gms of dimethylformamide and heated to 130°–135° C. for 2 hours. Dimethylformamide was recovered by vacuum stripping to 110° C. at 10 mm Hg. The residue was clarified by filtration yielding 370.0 gms of yellow oil (95.0% of theoretical). The product is soluble in benzene and acetone. The structure is believed to be:

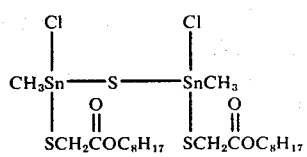

Cl — 9.4% (calculated 9.12%)
S — 11.9% (calculated 12.3%)

EXAMPLE 3

A mixture of 0.1 M of dimethyltin sulfide, 0.1 M of benzyl chloride and 40 gms of dimethylformamide was heated to 130°–135° C. for 2 hours. After stripping to 110° C. at 10 mm Hg there remained 30.5 gms of pale yellow oil. The theoretical yield is 30.7 gms for:

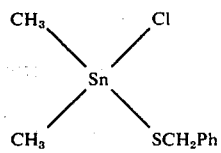

S — 10.2% (calculated 10.4%)
Cl — 11.6% (calculated 11.5%)

EXAMPLE 4

A mixture of 0.1 M of dimethyltin sulfide, 0.1 M of 2-chloroethyloctoate and 40 gms of dimethylformamide was heated under an atmosphere of nitrogen for 4 hours at 150° C. After stripping to 120° C at 10 mm Hg and filtering to clarify, there was obtained 34.2 gms of yellow oil. The theoretical yield is 39.7 gms for:

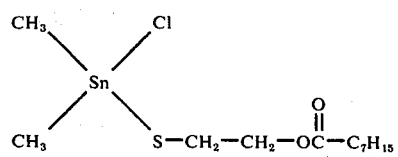

Cl — 8.6% (calculated 8.94%)
S — 8.3% (calculated 8.06%)

EXAMPLE 5

One-half mole of dimethyltinsulfide was mixed with 0.5 M of isooctyl-3-chloropropionate and 75 grams of dimethylacetamide and heated at 145°–155° C. for 4 hours. After stripping to 120° C. at 10 mm Hg and filtering to clarify, there was obtained 194.6 grams of a yellow oil. The theoretical yield is 200.7 grams for:

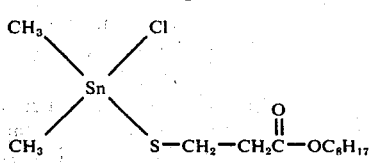

Cl — 8.5% (calculated 8.84%)
S — 8.1% (calculated 7.98%)

EXAMPLE 6

A mixture of 0.1 M of dimethyltin sulfide, 0.1 M of isooctylchloroacetate and 40 gms of dimethylsulfoxide was heated under nitrogen at 130° C. for 1.5 hours. After stripping to 110° C. at 10 mm Hg there remained 32.0 gms of red oil.

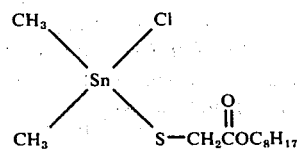

S — 8.5% (calculated 8.26%)

EXAMPLE 7

A mixture of 0.1 M of dimethyltinsulfide, 0.1 M of isooctylchloracetate and 30 gms of tris(dimethylamino) phosphine oxide was heated at 130° C. for 2 hours. After stripping to 120° C. at 1.0 mm Hg there remained 37.1 gms of yellow oil.

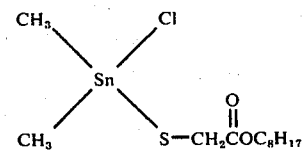

— 9.3% (calculated 9.16%)

EXAMPLE 8

A mixture of 0.2 M of dibutyltin sulfide, 0.2 M of isooctylchloroacetate and 40.0 gms of dimethylformamide was heated under $N_2$ for 2 hours at 130°–135° C. after stripping and filtering there was obtained 93.8 gms of yellow liquid. The theoretical yield is 94.3 gms for:

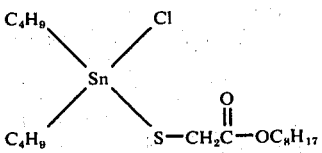

Cl — 7.2% (calculated 7.51%)
S — 6.5% (calculated 6.77%)

EXAMPLE 9

A mixture of 0.1 M of monobutyltin sulfide

0.2M of isooctylchloroacetate and 40.0 gms of dimethylformamide was heated under nitrogen to 130°–135° C. for 2 hours. After stripping to 120° C at 10 mm Hg there was obtained 83.7 gms of viscous amber oil. The theoretical yield is 86.1 gms for:

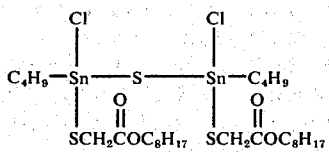

Cl — 8.0% (calculated 8.22%)
S — 10.7% (calculated 11.1%)

EXAMPLE 10

A mixture of 0.1 M of bis(tributyltin) sulfide, 0.1 M of isooctylchloroacetate and 20 gms of dimethylformamide was heated for 2 hours at 130°–135° C. After stripping and filtering there remained 91.3 gms of yellow oil.

Cl — 4.1% (calculated 4.32%).

(4) 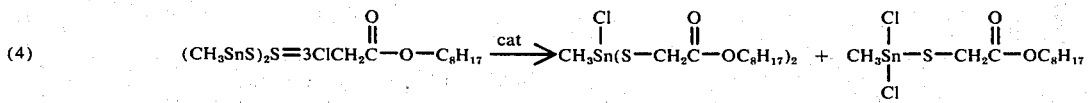

EXAMPLE 11

A mixture of 0.1 M of dimethyltin sulfide, 0.1 M of isooctylbromoacetate and 20.0 gms of dimethylformamide was heated under nitrogen for 2 hours at 130°–135° C. After stripping to 110° C. at 10 mm Hg there remained 37.8 gms of yellow oil. The theoretical yield is 43.2 gms for:

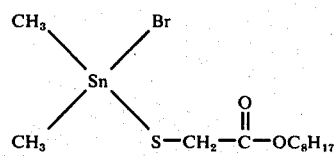

Br — 17.9% (calculated 18.5%)

EXAMPLE 12

A mixture of 0.1 M of dimethyltin sulfide, 0.1 M of benzylbromide and 30 gms of dimethylformamide was heated to 130° C. for 2 hours. After stripping there remained 33.8 gms of yellow oil. The theoretical yield is 35.2 for:

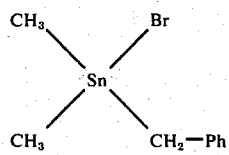

Br — 21.9% (calculated 22.7%)

Example 13 demonstrates the lack of reaction in the absence of catalyst.

EXAMPLE 13

One-tenth mole of dimethyltin sulfide was mixed with one-tenth mole of isooctylchloroacetate and heated under nitrogen. At 90° C., solution of the solid dimethyltin sulfide was complete and a clear, nearly colorless liquid resulted. After a 2-hour reaction period of 130°–135° C, the reaction mixture was cooled. At 90° C, precipitation of unreacted dimethyltin sulfide began. Precipitation was completed by cooling to 20° C. The unreacted dimethyltin sulfide was removed by filtration and freed of isooctylchloroacetate by washing with heptane. Ninety-seven percent of the starting dimethyltin sulfide was recovered unchanged.

EXAMPLE 14

One-half mole of monomethyltin sulfide $(CH_3SnS)_2S$ was mixed with 1.5 M of isooctylchloroacetate and 150 gms of N-methyl-2-pyrrolidone and heated to 130°–135° C. for 2 hours. The N-methyl-2-pyrrolidone was recovered by vacuum stripping to 120° C. at 10 mm Hg. The residue was clarified by filtration yielding 465 gms of amber oil (94.6% of theoretical).

Sulfur — 9.6% found (9.76% calculated);
Chlorine — 10.9% found (10.82% calculated).

The postulated reaction is:

As shown in Example 14 by varying the mole ratio of monoorganotin sulfide to $R_1X$ compound from 1:2 to 1:3 the products obtained are changed. In place of the $(CH_3SnS)_2S$ in Example 14 there can be used any of the other compounds of the formula

$(R Sn)_2 S$ set forth above an in place of the isooctyl chloroacetate there can be and any of the other compounds of the formula $R_1X$ set forth above.

Thus in reaction (4) there can be used for example:
37. monomethyltin sulfide + 3 methyl chloroacetate + 3 dimethyl formamide (catalyst)
38. monooctyltin sulfide + 3 methyl bromoacetate + 4 dimethyl acetamide (catalyst)
39. monooctadecyltin sulfide + 3 isodecyl chloroacetate + 3 diethyl formamide (catalyst)
40. monobenzyltin sulfide + 3 butyl chloroacetate + 3 diethyl sulfoxide (catalyst)
41. monophenyltin sulfide + 3 cyclohexyl chloroacetate + 3 dimethyl sulfoxide (catalyst)
42. monoallyltin sulfide + 3 benzyl chloroacetate + 3.5 tris(dimethylamino) phosphine oxide (catalyst)
43. monomethyltin sulfide + 3 2-chloroethyl stearate + 3 dimethyl acetamide (catalyst)
44. monobutyltin sulfide + 3 2-chloroethyl oleate + 2.5 dimethyl formamide (catalyst)
45. monocyclohexyltin sulfide + 3 2-chloroethyl butyrate + 3 dimethyl formamide (catalyst)
46. monomethyltin sulfide + 3 2-chloroethyl methacrylate + 3 dimethyl formamide (catalyst)
47. Monomethyltin sulfide + 3 hexyl 3-chloropropionate + 3 N-methyl pyrrolidone (catalyst)
48. monobutyltin sulfide + 3 allyl bromide + 4 dimethyl formamide (catalyst)

I claim:

1. A process of preparing an organotin halide mercaptide or a mixture of an organotin halide and an organotin mercaptide from an organotin sulfide comprising reacting:

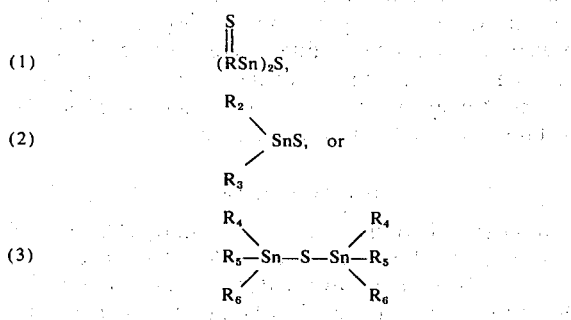

with a compound of the formula $R_1X$ in the presence of a catalyst having the formula:

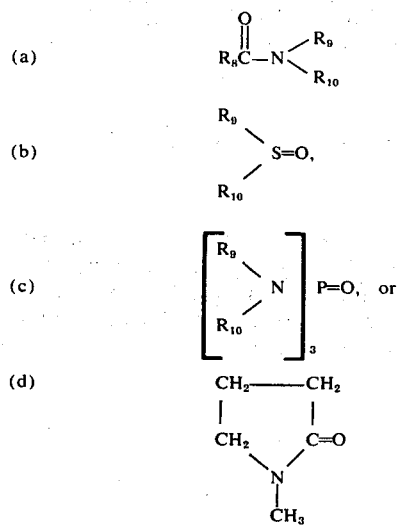

where $R$, $R_2$, $R_3$, $R_4$, $R_5$, and $R_6$ are alkyl, cycloalkyl, alkenyl, aryl or aralkyl, $R_1$ is $$-(CH_2)_nC(O)-OR_7, \quad -CH_2CH_2OC(O)R_{12}, \quad CH_2=C(R_{11})-CH_2,$$

or benzyl, $R_7$ is alkyl, cycloalkyl, alkenyl, or aralkyl, $R_{12}$ is alkyl or alkenyl, X is halogen of atomic weight 35 to 80, $n$ is 1 or 2, $R_8$ is hydrogen or methyl, $R_9$ and $R_{10}$ are alkyl of 1 to 2 carbon atoms and $R_{11}$ is hydrogen or methyl, with the proviso that when compound (1) is reacted the product is the reaction product of either 2 moles of $R_1X$ with 1 mole of compound (1) or the product is the reaction product of 3 moles of compound (1) with 1 mole of $R_1X$, when compound (2) is reacted the product is the reaction product of 1 mole of compound (2) with 1 mole of $R_1X$ and where compound (3) is reacted the product is the reaction product of 1 mole of compound (3) with 1 mole of $R_1X$.

2. A process according to claim 1 wherein the reaction is carried out at a temperature at which the reaction proceeds up to the boiling point of the catalyst.

3. A process according to claim 2, wherein the temperature is 130° to 155° C. and the catalyst is used in an amount of 0.8 to 8 moles per mole of starting organotin sulfide.

4. A process according to claim 2 wherein the temperature is from 100° C. to the boiling point of the catalyst and R, $R_2$, $R_3$, $R_4$, $R_5$ and $R_6$ are alkyl of 1 to 20 carbon atoms, cycloalkyl having 5 to 6 carbon atoms in the ring, alkenyl of 2 to 20 carbon atoms, phenyl, alkylphenyl having up to 4 carbon atoms in the alkyl group, $R_7$ is alkyl of 1 to 20 carbon atoms, cycloalkyl having 5 to 6 carbon atoms in the ring, alkenyl of 2 to 20 carbon atoms or benzyl, $R_{12}$ is alkyl of 1 to 19 carbon atoms or alkenyl of 2 to 17 carbon atoms.

5. A process according to claim 4 wherein X is chlorine.

6. A process according to claim 4 wherein the solvent is dimethyl formamide.

7. A process according to claim 4 wherein R is alkyl of 1 to 8 carbon atoms.

8. A process according to claim 4 comprising reacting 1 mole of

with 2 moles of $R_1X$.

9. A process according to claim 4 comprising reacting 1 mole of

with 3 moles of $R_1X$ to form

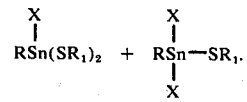

10. A process according to claim 4 comprising reacting 1 mole of

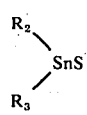

with 1 mole of $R_1X$ to form

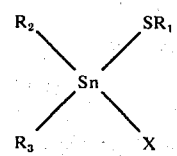

11. A process according to claim 4 comprising reacting 1 mole of

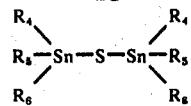

with 1 mole of $R_1X$ to form

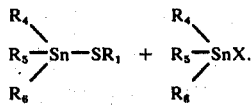

12. A process according to claim 4 wherein R is alkyl of 1 to 8 carbon atoms and $R_1$ is

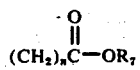

where $R_7$ is alkyl of 6 to 18 carbon atoms.

13. A process according to claim 4 wherein R is alkyl of 1 to 8 carbon atoms and $R_1$ is

14. A process according to claim 4 wherein R is alkyl of 1 to 8 carbon atoms and $R_1$ is allyl or methallyl.

15. A process according to claim 4 wherein R is alkyl of 1 to 8 carbon atoms and $R_1$ is benzyl.

16. A compound having the formula

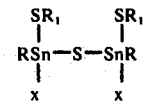

where R is alkyl, cycloalkyl, alkenyl, aryl, or aralkyl,

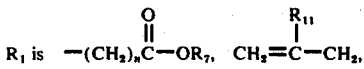

or benzyl, $R_7$ is alkyl, cycloalkyl, alkenyl or aralkyl, $R_{11}$ is hydrogen or methyl and $R_{12}$ is alkyl or alkenyl, n is 1 or 2 and x is halogen of atomic weight 35 to 80.

17. A compound according to claim 16 wherein $R_1$ is

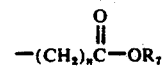

where $R_7$ is alkyl, cycloalkyl, alkenyl or aralkyl and n is 1 or 2.

18. A compound according to claim 16 wherein $R_1$ is allyl or methallyl.

19. A compound according to claim 16 wherein $R_1$ is benzyl.

* * * * *